(12) United States Patent
Gratton et al.

(10) Patent No.: US 6,192,261 B1
(45) Date of Patent: *Feb. 20, 2001

(54) PHOTOSENSOR WITH MULTIPLE LIGHT SOURCES

(75) Inventors: Enrico Gratton; Sergio Fantini; Maria Angela Franceschini, all of Urbana; William Mantulin; Beniamino Barbieri, both of Champaign, all of IL (US)

(73) Assignee: I.S.S. (USA), Inc., Champaign, IL (US)

(*) Notice: Under 35 U.S.C. 154(b), the term of this patent shall be extended for 0 days.

This patent is subject to a terminal disclaimer.

(21) Appl. No.: 09/072,912

(22) Filed: May 4, 1998

Related U.S. Application Data

(62) Division of application No. 08/564,439, filed on Nov. 29, 1995, now Pat. No. 5,772,587, which is a division of application No. 08/168,813, filed on Dec. 16, 1993, now Pat. No. 5,497,769, and a division of application No. 08/253,935, filed on Jun. 3, 1994, now Pat. No. 5,492,118.

(51) Int. Cl.[7] .................................................. A61B 5/00
(52) U.S. Cl. ............................................ 600/310; 600/322
(58) Field of Search ........................... 600/310, 322–324; 356/71

(56) References Cited

U.S. PATENT DOCUMENTS

| | | |
|---|---|---|
| 4,840,485 | 6/1989 | Gratton . |
| 4,854,699 | 8/1989 | Edgar, Jr. . |
| 4,972,331 | 11/1990 | Chance . |
| 5,032,024 | 7/1991 | Cope . |
| 5,057,695 | 10/1991 | Hirao et al. . |
| 5,122,974 | 6/1992 | Chance . |
| 5,167,230 | 12/1992 | Chance . |
| 5,187,672 | 2/1993 | Chance et al. . |

(List continued on next page.)

FOREIGN PATENT DOCUMENTS

| | | |
|---|---|---|
| 2228314A | 2/1989 | (GB) . |
| 0 497 021 A1 | 8/1992 | (JP) . |
| WO 90/09003 | 8/1989 | (WO) . |
| WO 94/10901 | 5/1994 | (WO) . |

OTHER PUBLICATIONS

Article entitled: Time–Resolved Spectroscopy of the Human Forearm by Ferrari et al.—J. Photochem, Photobiol. B: Biol., 16 (1992) 141–153.

Article entitled: "Tissue Characterization and Imaging Using Photon Density Waves" by Svaasand et al.—Optical Engineering, Feb., 1993, vol. 32 No. 2, pp. 258–265.

Article by J.R. Lakowicz et al. entitled: Frequency–domain fluorescence spectroscopy, a new method for the resolution of complex fluorescence emission, from Trends in Analytical Chemistry, Nov., 1986, pp. 257–263.

(List continued on next page.)

Primary Examiner—Robert L. Nasser
(74) Attorney, Agent, or Firm—Garrettson Ellis Seyfarth Shaw

(57) ABSTRACT

The quantitative determination of various materials in highly scattering media such as living tissue may be determined in an external, photometric manner by the use of a plurality of light sources positioned at differing distances from a sensor. The light from said sources is amplitude modulated, and, in accordance with conventional frequency domain fluorometry or phosphorimetry techniques, the gain of the sensor is modulated at a frequency different from the frequency of the light modulation. Data may be acquired from each of the light sources at differing distances at a frequency which is the difference between the two frequencies described above. From these sets of data from each individual light source, curves may be constructed, and the slopes used to quantitatively determine the amount of certain materials present, for example glucose, oxyhemoglobin and deoxyhemoglobin in living tissue.

19 Claims, 6 Drawing Sheets

U.S. PATENT DOCUMENTS

| | | |
|---|---|---|
| 5,188,108 | 2/1993 | Secker . |
| 5,209,231 | 5/1993 | Cote et al. . |
| 5,212,386 | 5/1993 | Gratton et al. . |
| 5,213,105 | 5/1993 | Gratton et al. . |
| 5,243,983 | 9/1993 | Tarr et al. . |
| 5,267,152 | 11/1993 | Yang et al. . |
| 5,267,715 | 12/1993 | Yang et al. . |
| 5,331,958 | 7/1994 | Oppenheimer . |
| 5,348,003 | 9/1994 | Caro . |
| 5,353,799 * | 10/1994 | Chance ................................ 600/323 |
| 5,402,778 | 4/1995 | Chance . |
| 5,515,847 | 5/1996 | Braig et al. . |
| 5,517,987 | 5/1996 | Isuchiya . |
| 5,553,614 | 9/1996 | Chance . |
| 5,564,417 | 10/1996 | Chance . |
| 5,770,631 * | 7/1998 | Chance ................................ 600/323 |
| 5,772,587 * | 6/1998 | Gratton et al. ...................... 600/310 |

OTHER PUBLICATIONS

Article by Patterson et al. by Applied Optics, vol. 30, No. 31, pp. 4474–4476 entitled: Frequency–Domain Reflectance for the Determination of the Scattering and Absorption Properties of Tissue, Nov. 1, 1991.

Article by Patterson et al. by Applied Optics, vol. 28, No. 12, pp. 2331–2336 entitled: "Time Resolved Reflectance and Transmittal for the Non–Invasive Measurement of Tissue Optical Properties", Jun. 15, 1989.

* cited by examiner

PHOTOSENSOR WITH MULTIPLE LIGHT SOURCES

CROSS REFERENCE TO RELATED APPLICATIONS

This is a division of the Gratton et al. U.S. application Ser. No. 08/564,439, filed Nov. 29, 1995, now U.S. Pat. No. 5,772,587 which, in turn, is a division of the Gratton et al. U.S. application Ser. No. 08/168,813, filed Dec. 16, 1993, now U.S. Pat. No. 5,497,769 and Ser. No. 08/253,935, filed Jun. 3, 1994, now U.S. Pat. No. 5,492,118.

BACKGROUND OF THE INVENTION

The determination of the optical properties of tissues is of fundamental importance in many fields of medicine, both for diagnostic and monitoring purposes. It is well known that light of differing wavelengths penetrates differently in various tissues. In the near infrared region, for example, (about 650 nm to about 1000 nm), light of this wavelength penetrates several centimeters through tissue. It is intended that the term "light" includes other electromagnetic radiation as well which is invisible to the human eye, for example, infrared and ultraviolet.

Because of the capability of various forms of light to penetrate tissue for several centimeters, photometric or spectroscopic methods can be used to measure the concentration of tissue metabolites such as hemoglobin by the measuring of the absorption of the light at one or more wavelengths. It is desirable and important that apparatus which measures the optical properties of tissues for clinical purposes provide quantitative information of a desired parameter, for example the concentration of oxyhemoglobin, or deoxyhemoglobin, glucose, or other metabolites. Also knowledge of concentrations of materials such as glucose present in tissue can be very valuable.

In normal practice, the absolute determination of the concentration of a substance can be obtained by the measurement of the light transmitted through a sample of known thickness. Such a transmission measurement enables one to determine the absorption coefficient. Using this, the concentration of the measured substance can be calculated using the molar extinction coefficient of that substance via the Beer-Lambert law.

In the event of interference caused by more than one substance being present, measurement at different wavelengths can provide a method to determine the concentration of one or more different chemical species present, assuming that the materials present have different absorption spectra. The success of this method depends on the precision of the measurement and on the number of different substances present.

Additional problems arise in the photometry of tissues and other materials having high turbidity, such as emulsions. For purposes of this disclosure, it is to be understood that the term "tissue" includes living materials, but can also include non-living materials such as emulsions when it is desired to obtain similar data from such emulsions as is done by this invention with tissues. A measurement of the light transmitted through a slab of tissue has in the prior art been not practical, using non-invasive methods, except for special, thin regions of the body where light can shine entirely through the tissue and be detected on the other side. An example of this is a clinically used photometric blood oxygen sensor, which fits on the finger tip and shines directly therethrough to give real time oxygen concentration data.

In tissue photometry, the amount of transmitted light depends not only on the absorption of the medium being analyzed, but also on the scattering properties thereof. This light scattering greatly increases the complexity of photometric analysis of tissue, emulsions, and similar materials, since light scattering produces an unpredictable variation of the amount of light transmitted, which can vary significantly between various samples of tissues and the like.

Many different methods have been proposed to deal with this problem of scattering in photometric processes. For example, empirical corrections based on the type of tissue to be measured have been used to account for the effect of scattering on the absorption properties. For reflection measurements, theoretical models have been used to calculate the albedo of a surface. The success of all of these models has been poor, although there are commercially available instruments based upon those principles. A major problem is that in order to obtain a reasonable estimate of the concentration of a substance in tissue, some sort of a priori calibration must be performed, based on a statistical analysis of a large number of corresponding tissue samples. However, the range of variation of scattering within tissues from various individuals results in fundamentally unpredictable results, with the photometric results being strongly modified by factors such as skin color, and the amount of lipids in muscles.

The Hamamatsu Company of Japan in 1990 introduced a simple tissue spectrometer called NIRO 500 for the measurement of tissue oxygenation and total blood volume for neonatal monitoring. The principles of this device are as disclosed in Cope U.S. Pat. No. 5,032,024. The instrument is a steady state instrument, and is based on four different laser diodes emitting in the near infrared range. The light is brought to the tissue using a fiber optic system. The measurement is purely a steady-state one, with the optical path length in the tissue being not measurable. Thus, contrary to this invention, only relative quantities can be obtained, rather than absolute concentrations of oxy-and deoxyhemoglobin.

By this invention, absolute quantities of materials found admixed in highly turbid media may have their concentrations determined in a quantitative manner. Specifically, by this invention tissue metabolites may be quantitatively determined in real time, on a continuous basis, for example, concentrations of oxy- and deoxy-hemoglobin. This can be accomplished without the need to pass light through a narrow portion of tissue, for example an extremity such as the finger. Rather, a sensor may be placed on a more central area of the body for determination of metabolite concentrations or other parameters there. This may be accomplished in a non-invasive manner, essentially instantaneously. Also, it may be possible for different metabolites present to be selectively and quantitatively determined on an essentially instantaneous basis. Also, materials such as glucose may have their relative concentrations determined in tissue and other turbid media.

DESCRIPTION OF THE INVENTION

In accordance with this invention, one may analyze for the presence and concentration of a substance in a highly turbid medium such as tissue of a patient by the steps of: illuminating one or more light sources which are spaced at different distances from one or more light sensors, while modulating the intensity of light from said light source or sources at a first frequency and passing said modulated light through the turbid sample for testing and then to the respective sensor or sensors, so that each sensor receives a light signal or signals that pass a different distance through the turbid medium. The critical thing is the use of a plurality of light paths of differing lengths, irrespective of the numbers of sensors and light sources used to create them. This may be accomplished without a step of comparing the beams of light which traverse the turbid medium with the beams of the light as emitted prior to traversing said medium.

One also provides a signal coherent with the modulated light, at a second frequency, to the light sensor or sensors, to modulate the gain of, or multiply the output of, the light sensors by the coherent signal, the second frequency being different from the first frequency. One then derives a resultant signal from each of the sensors while receiving the modulated light, the resultant signal being at a frequency of the difference between the first and second frequencies. From this, it becomes possible to detect at least two of the following characteristics of the modulated light sensed by the sensor or sensors: the phase shift component, the DC component, and the AC component.

The terms "DC component" and "AC component" define differing portions of the amplitude of the light from the light sources. Specifically, as previously described, the light from the light sources is of amplitude modulated intensity, so that it becomes brighter and dimmer in a cycle at the first frequency. This frequency is typically very high (e.g. 80 to 200 MHz) so that the fluctuation of light intensity is invisible to the eye. The AC component of the light comprises the change in light intensity from the peak of the cycle to the trough of the cycle; that is, the maximum change in the amplitude of the light intensity as it goes through its rapid cycle of amplitude modulation. The DC component is that portion of the light intensity measured from zero to the minimum intensity that the light always possesses, which of course is found at the bottom of the troughs of the wave pattern imposed on the light by the amplitude modulation.

Therefore, the maximum intensity of the light signal, found at the top of each wave, is the sum of the DC and AC light components. The minimum intensity of the light in its amplitude modulated cycle is the DC component alone.

In accordance with this invention, as the amplitude modulated light passes through human tissue or another highly turbid material to the sensor, the phase of the amplitude modulated light signal will shift, and the DC and AC components will attenuate. From this information, it is possible to obtain quantitative information as to the concentrations of certain materials present in the tissue on a real time or moment-by-moment basis.

This may be accomplished by sequentially turning on and off the plurality of light sources or light sensors, which are at differing distances from each other. Thus, by the data provided by passing light through each of these differing tissue distances, differing values for phase shift, DC component, and/or AC component may be determined separately for the light path between each light source and sensor, to compute linear graphical data having characteristic slopes. Once the slopes are known, the values of scattering and absorption coefficients at the wavelength of the light used can be computed. From these values, particularly at two different wavelengths, absolute concentrations of materials present such as oxyhemoglobin or deoxyhemoglobin, can be calculated, as can relative concentrations of glucose, for example. Once the concentrations of oxyhemoglobin and deoxyhemoglobin are known, for example, the oxygen saturation and the blood volume of a patient can be calculated.

This can be accomplished in very short order through a microprocessor or the like, so that these values can be displayed in real time to a physician or nurse simply by applying a sensor head to the skin of a patient, without any need for the light to pass entirely through the tissue of the patient to the other side.

Alternatively, one or more light sources, such as modulated laser diodes, may direct light to multichannel fiber optic switches, for example, which in turn can direct the light to a plurality of output channels. Each of these channels may be connected to a fiber bringing light to a single light sensor, or more than one if desired. A switch then is used to provide sequential passage of the light through the respective channels and optical fibers, the fibers being positioned to provide the variable distance from the light sensor or sensors used in this invention, to provide equivalent results to the above.

The sensor for detecting light in this invention can detect scattered light in the tissue, so that the light paths from the light sources to the sensor do not have to be linear. In fact, the direction of light emission and the general direction of light sensing may be parallel, as illustrated by the specific embodiment of the sensor head disclosed herein.

Preferably, the sensor for detecting light used herein may also carry the light source or sources in a common sensor head along with the sensor or sensors, plus a shield to prevent the direct access of light from the light source or sources to the light sensor or sensors without passing through the tissue of the patient.

The sensor instrument of this invention may carry an electronic processor for computing the slopes of at least two of the phase shift, the DC, and the AC components which are provided by separate signals from each of the plurality of light sources of differing distances. From this, the processor can also compute the scattering and absorption coefficients of the tissue. From this, for example, the absolute concentrations of at least one of oxyhemoglobin and deoxyhemoglobin present in the tissue may be computed from typically the absorption coefficient. The sensor instrument may then have an apparatus for displaying such concentration or concentrations as a real time value.

The intensity of the light from the light source or sources may preferably be amplitude modulated at about 50 to 150 MHz. The second frequency of the second signal is of the same order, but differing from the first frequency typically by about 10 Hz to 100 KHz.

Typically, the light which is used is of a wavelength of about 650 nm to about 1000 nm, with at least three tissue light paths of differing distances being present. However, it is preferred for at least six light paths of differing distances to be present, with the light sources or sensors being disposed in a pair of rows to provide pairs of groups of light sources or sensors in the respective rows of the same distance to provide similar light paths. This permits the simultaneous gathering of data at different light wavelengths, which different light wavelengths are emitted each by one of the rows or groups of the sensors. In other words, a first group of light paths of differing distances is provided by a light source or sources and a light sensor or sensors, all of the light being at one wavelength for calculation of slopes of at least two of the phase shift, DC and AC at that frequency. Then, a second group of light paths of differing distances may be provided, optionally for improvement of the data, in similar manner at a different light wavelength to determine a second set of slopes of at least two of the phase shift, DC and AC for that second wavelength. Also by this means, the absolute concentration of two unknowns can be simultaneously calculated, e.g. deoxyhemoglobin and oxyhemoglobin, particularly where each light wavelength represents a prominent absorption area of one of the unknown materials, while not being strongly absorbed by the other of the unknown materials, each separate wavelength being strongly absorbed by a different one of the unknown materials.

It is also preferred for each of the plurality of light paths to be sequentially activated (illuminated) for a length of time that is an exact multiple of a wave having a frequency which comprises the difference between the first and second frequencies as described above (the "cross correlation frequency").

Also, the information sensed through the light paths may be summed and averaged from about eight to about eight hundred times of repetition, to obtain an intensified average of the photometric information received from each light source.

Typically, the method and apparatus of this invention make use of principles of frequency domain fluorometry and/or phosphorimetry which are well known, being disclosed for example in Gratton U.S. Pat. No. 4,840,485, Gratton et al. U.S. Pat. Nos. 5,212,386, and 5,323,010, among others.

DESCRIPTION OF SPECIFIC EMBODIMENTS

Figure 1:
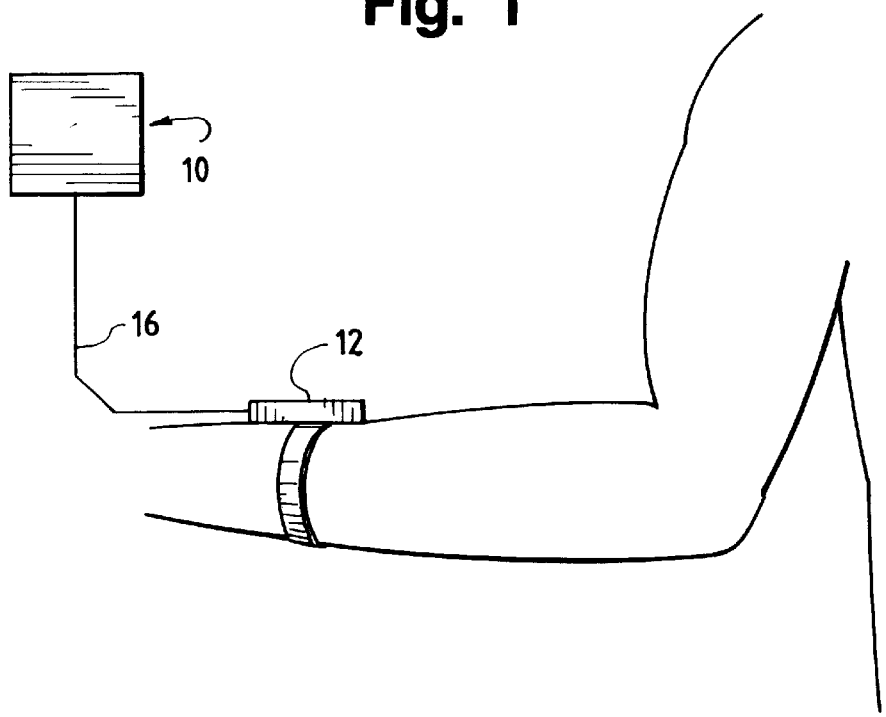
FIG. 1 is an elevational view of the sensor instrument of this invention, shown attached to the arm of a patient for sensing parameter of body tissue.
Figure 2:
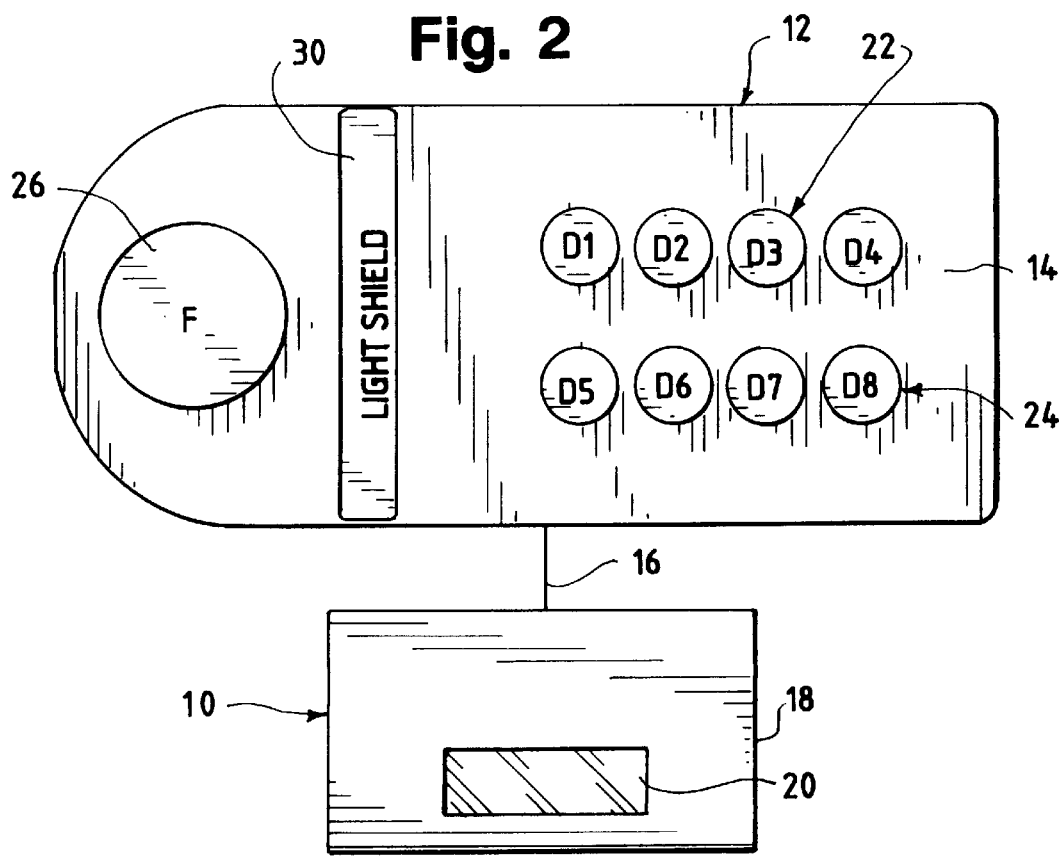
FIG. 2 is a schematic bottom plan view of the sensor instrument of FIG. 1, showing details of the sensor head.

In the drawings, a sensor instrument is shown for non-invasively and quantitatively determining the real time concentration of oxyhemoglobin and deoxyhemoglobin within living tissue of the patient. Sensor instrument 10 comprises a sensor head 12, which comprises a body having a sensor face 14 which may be flat or curved for better contact with the contour of a patient's arm, thigh, chest, or the like. Sensor 12 is placed with sensor face 14 in intimate contact with the skin of the patient. Cable 16 contains both an optical fiber and the electrical wires to convey both optical and electronic signals to processor unit 18. Alternatively, the light detector may be placed on the sensor head, and cable 16 is free of optical fibers. Data may be displayed at a readout window 20 in conventional manner.

Sensor head 12 carries eight light sources 22, 24 (individually labelled $D_1$–$D_8$) with four each of the respective light sources 22 and 24 being positioned in separate rows so that the respective light sources 22 and the respective light sources 24 are each at different distances from a conventional light sensor 26. Light sources 22, 24 may be light emitting diodes, laser diodes, or any other light source system which is capable of being amplitude modulated at the desired frequency range. Also, the wavelengths of the light sources are chosen to maximize the difference in light absorption in this specific embodiment of the oxyhemoglobin and deoxyhemoglobin species, specifically 700–900 nm.

Figure 4:
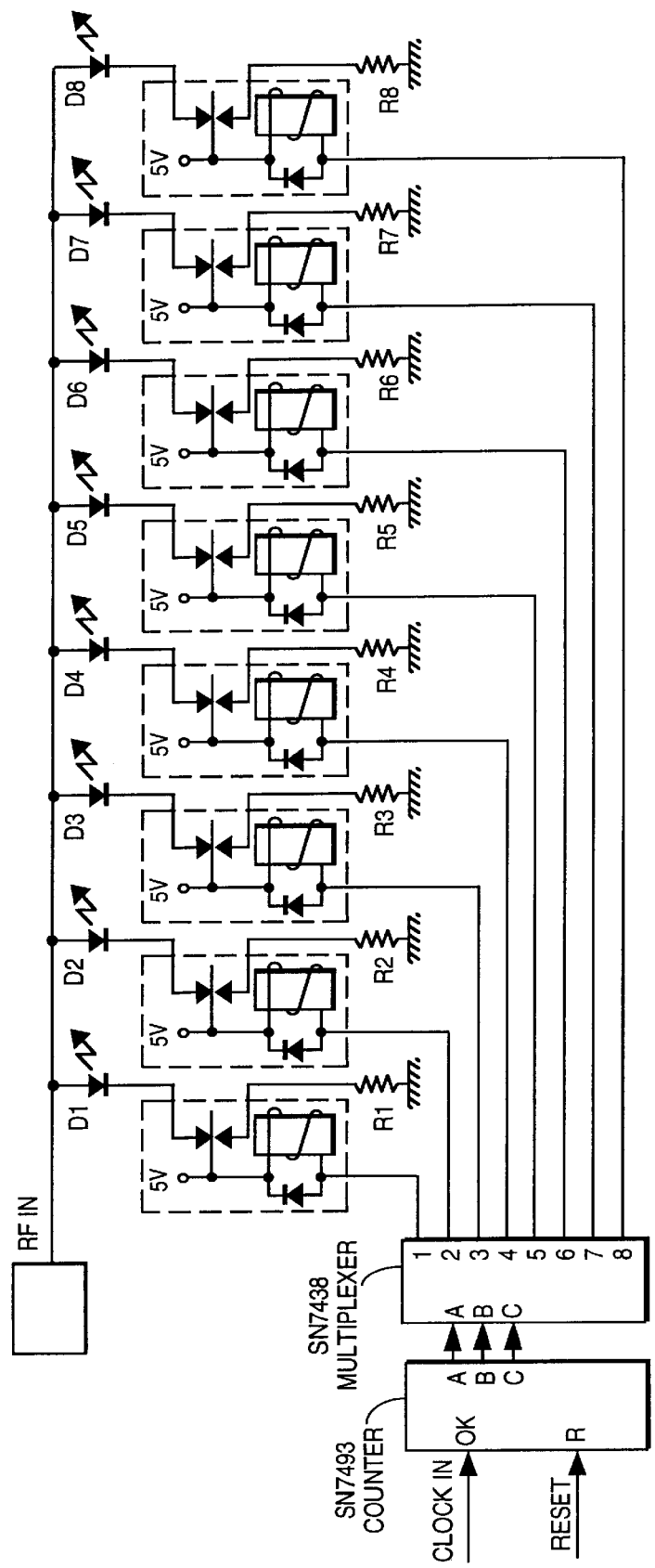
FIG. 4 is a diagram of a multiplexer circuit for turning the multiple light sources on and off in sequence, while causing the light emitted to be amplitude modulated at a high frequency.

By the multiplexer circuit of FIG. 4, the respective light sources 22, 24 are turned on and off, one at a time, in rapid succession. In this embodiment, the light sources are sinusoidally (amplitude) modulated at 120 MHz, to provide a frequency that maximizes the modulation of the source, and the sensitivity of the slopes described above to the scattering and absorption coefficients. Also, detectors or sensors 26 having good sensitivity at this frequency are readily available. Likewise, for hemoglobin detection, such a frequency provides a maximum signal-to-noise ratio.

Modulated light signals from the respective light sources 22, 24 enter the tissue of the patient, and travel in a highly scattered manner through the tissue of the patient to sensor 26. The direct transmission of light from each light source 22, 24 to sensor 26 without passing through tissue is prevented by a rubber light shield barrier 30, which projects slightly outwardly from face 14 of sensor head 12.

Figure 3:
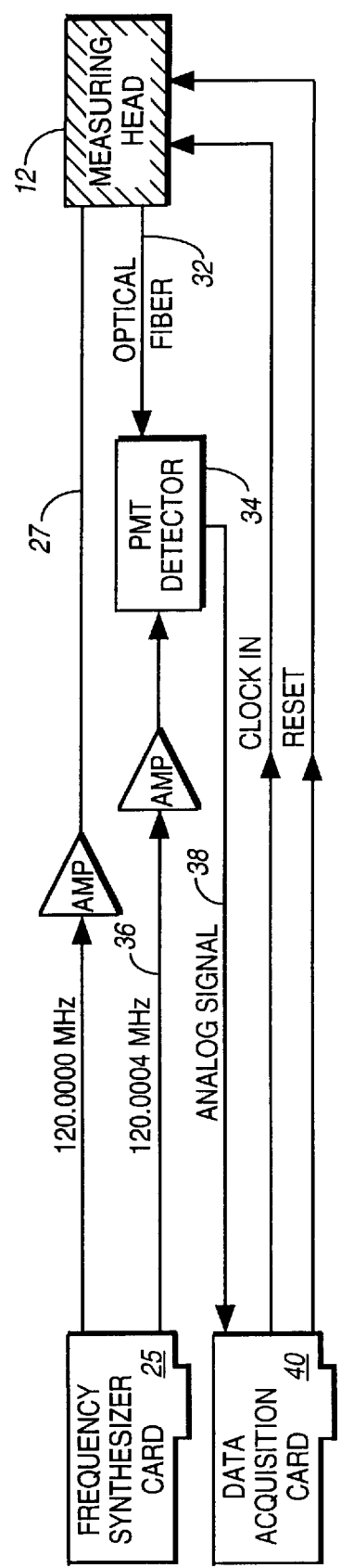
FIG. 3 is a block diagram of the electronics of the sensor instrument of the previous drawings.

The light passing through the tissue which is sensed by sensor 26 may be transmitted by an optical fiber 32 (FIG. 3), within connecting cable 16, which cable also carries wires, each communicating between sensor head 12 and processor unit 10. Light from optical fiber 32 passes to a photomultiplier detector 34.

Frequency synthesizer card 25 carries a frequency generator to provide an RF signal to head 12 and LEDs 22, 24 through wire 27 (also in cable 16), with conventional circuitry, to impose on the respective LEDs 22, 24 an amplitude modulation of 120.0000 MHz., which is the first frequency described above.

Frequency synthesizer card 25 also carries a frequency synthesizer which sends a second signal, coherent with the first but modulated at a second frequency, of 120.0004 MHz, through wire 36 to modulate the gain of photomultiplier detector 34. Thus, an analogue signal, which is a function of the signals through fiber 32 and wire 36, may be sent from detector 34 along wire 38 to data acquisition card 40. The particular analogue signal sensed by data acquisition card 40 may at be the "cross correlation frequency", which is the frequency of the difference between the first and second signals, or 400 Hz. in this example. This well established method produces a beating of the 120 MHz modulated current in the detector photomultiplier with the 120.0004 MHz radio frequency signal injected at the photomultiplier dynode, the photomultiplier output through wire 38 being modulated at the 400 Hz cross-correlation frequency. The radio frequency harmonics may be rejected by a low pass filter at an amplifier in detector 34.

Thus, each light source 22, 24 may be turned on for a length of time that is an exact multiple of the 400 Hz cross-correlation frequency wave period, i.e. for a length of time which is 2.5 milliseconds or a multiple thereof. In a typical measurement, a minimum of 8 to about a maximum of 800 periods of the 400 Hz wave are collected, depending on the light intensity through the tissue obtained at sensor 26. Each of these measuring periods may be digitized sixteen times. All of the collected waves of a measuring period may be averaged together, giving an average wave comprising 16 points, similar to the process described in Gratton et al. U.S. Pat. No. 5,212,386. Then, the 16 point wave may be transformed using a fast Fourier transform algorithm to give the value of the phase shift (P) component, the direct current (DC) component, and/or the alternating current (AC) component of the fundamental harmonic frequency of 400 Hz.

The above process can be repeated for each of light sources 22 and 24. The respective light sources 22 may emit at one wavelength such as 720 nm, and the other light sources 24 may emit at another wavelength such as 850 nm, to obtain a double set of data. Each of the respective light sources 22 are at different distances from sensor 26, as are each of the light sources 24, so that the data of each of the individual light sources of each set will be different, the more distant light sources exhibiting greater light attenuation through the tissue. The result of this can be a set of four values of the DC, AC, and phase shift (P) components at each wavelength, dependent on known distances of the light sources from the sensor.

Signals from the light detector 34 received by the data acquisition card 40 are digitized by the card (ISS A2D card, for example). A computer calculates from these data the respective slopes (S) of at least two of the DC, AC, and P components provided by each of the sets of lights 22, 24, since each of the respective lights provides differing values for the DC, AC, and P components, coupled with a known, constant distance of each light source from sensor 26. This can be accomplished as follows:

Mathematical Background

In a frequency domain spectrometer the light intensity is sinusoidally modulated at a frequency f, generally in the 100 MHz region. The light source generates a photon density wave in the strongly scattering medium that propagates at a reduced velocity with respect to the velocity of light in water. This is due to the large number of collisions of the photons composing the photon density wave with the particles in the medium. At every point in space, the light intensity varies sinusoidally at the same frequency of the source, but it is phase shifted and attenuated with respect to the intensity of the source. The phase shift P and the attenuation of the sinusoidal modulated intensity AC and also of the average light intensity DC are a function of the distance from the source r and of the scattering ($\mu_s$) and absorption ($\mu_a$) coefficients, plus DC, AC and P values. The following relationship holds, when both light sources 22, 24 and detector 26 are placed on the surface of a large, uniform medium such as a patient's arm:

$$DC = \frac{DC_o e^{-r\sqrt{2s}}}{r^2}$$

$$AC = \frac{AC_o e^{-r\sqrt{s}\sqrt{x+1}}}{r^2}$$

$$P = P_o + r\sqrt{s}\sqrt{x-1}$$

where $$s = \frac{3}{2}\mu_a(\mu_a + \mu_s)$$

$$x = \sqrt{y^2 + 1}$$

$$y = \frac{2\pi f}{v\mu_a}$$

In the above set of equations, the distance r between source and detector can be accurately measured independently. The first frequency of light modulation f is also exactly known, and v is the velocity of light in water. The only unknown parameters are the scattering and absorption coefficients, and phase, DC and AC factors of the modulated light.

The above equations require that we determine separately the value of the phase, DC and AC factors of the light. Rather than determining these quantities independently, it may be more practical to measure the values of the DC, AC and P at several distances r. The slopes of the plots of $\ln(r^2 DC)$, $\ln(r^2 AC)$ and P as a function of r provide quantities that are independent from the source constants. It is from these slopes that the scattering and absorption coefficients are measured in this particular implementation of the frequency domain spectrometer. By a measurement of any two of the above quantities, i.e., DC and P, AC and P and DC and AC, we can determine the optical parameters of the medium if we first determine the slopes of the plots defined above. Let us indicate with $S_{dc}$, $S_{ac}$, and $S_p$ the three slopes previously defined. The equations that relate $\mu_a$ and $\mu_s$ to the above slopes can be obtained from the following formulas:

$$\mu_a = \frac{2\pi f}{V}(X^2 - 1)^{-1/2}$$

(used for determining concentrations)

$$\mu_s = \frac{S^2}{2\mu_a} - \mu_a$$

(which may be used to determine imaging properties, see U.S. Pat. NO. 5, 213, 105.

Thus, the absorption and scattering coefficients can be measured independently.

The symbols X and S are defined as follows for the 3 different pairs of possible measurements.

Using AC and phase measurements $$X = \frac{S_{ac}^2 + S_p^2}{S_p^2 - S_{ac}^2}$$

$$S = \sqrt{S_{ac}^2 - S_p^2}$$

Using DC and phase measurements $$X = \frac{S_{dc}^2 + 2S_p^2}{S_{dc}^2}$$

and using DC and AC measurements $$X = \frac{2S_{ac}^2 - S_{dc}^2}{S_{dc}^2}$$

$$S = S_{dc}$$

Thus, $\mu_a$ and $\mu_s$ can be calculated by the above equations.

As stated above, any two out of the three slopes, once calculated as above by data acquisition card 40, may be used to electronically compute by card 40 the values of the scattering and absorption coefficients at each of the wavelengths used respectively by the lights 22 and 24. Preferably, the phase shift (P) slope and the DC slope are the values used for computing the scattering and absorption coefficients.

From these values, the absolute concentrations of oxyhemoglobin and deoxyhemoglobin can be calculated using the following relationships.

$$[O] = \frac{\mu_{a1}\epsilon_{d2} - \mu_{a2}\epsilon_{d1}}{\epsilon_{o1}\epsilon_{d2} - \epsilon_{o2}\epsilon_{d1}}$$

$$[D] = \frac{\mu_{a2}\epsilon_{o1} - \mu_{a1}\epsilon_{o1}}{\epsilon_{o1}\epsilon_{d2} - \epsilon_{o2}\epsilon_{d1}}$$

Where $\epsilon$ is the extinction coefficient, the subscript d1 represents the extinction coefficient of deoxyhemoglobin at the first wavelength (for example 720nm); the subscript d2 represents the extinction coefficient of deoxyhemoglobin at the second wavelength (for example 850 nm). The subscript o1 represents the same coefficient for oxyhemoglobin at the first wavelength. The subscript o2 represents the same coefficient for oxyhemoglobin at the second wavelength.

Extinction coefficients for hemoglobin at various wavelengths are available in the book by R. Lemberg and J. W. Legge entitled Hematin Compounds and Bile Pigments (Interscience, N.Y.) 1949. Specifically, the values for the various subscripts of epsilon are as follows: d1=921; d2=414; o1=230; o2=576, in units of $Mol^{-1}cm^{-1}$.

$\mu_{a1}$ and $\mu_{a2}$ are the respective absorption coefficients respectively at the first wavelength and the second wavelength for oxyhemoglobin and deoxyhemoglobin, dependent on the equation.

It can be seen that the above equations require the use of two different wavelengths of light, which can be emitted respectively from light sources 22 and light sources 24 as previously described.

From the above concentrations of the oxy and deoxy species, the oxygen saturation and the blood volume can be obtained using the following relationships.

Oxygen saturation of hemoglobin=100%[O]/[O]+[D]);

Total hemoglobin=[O]+[D]

Figure 5:
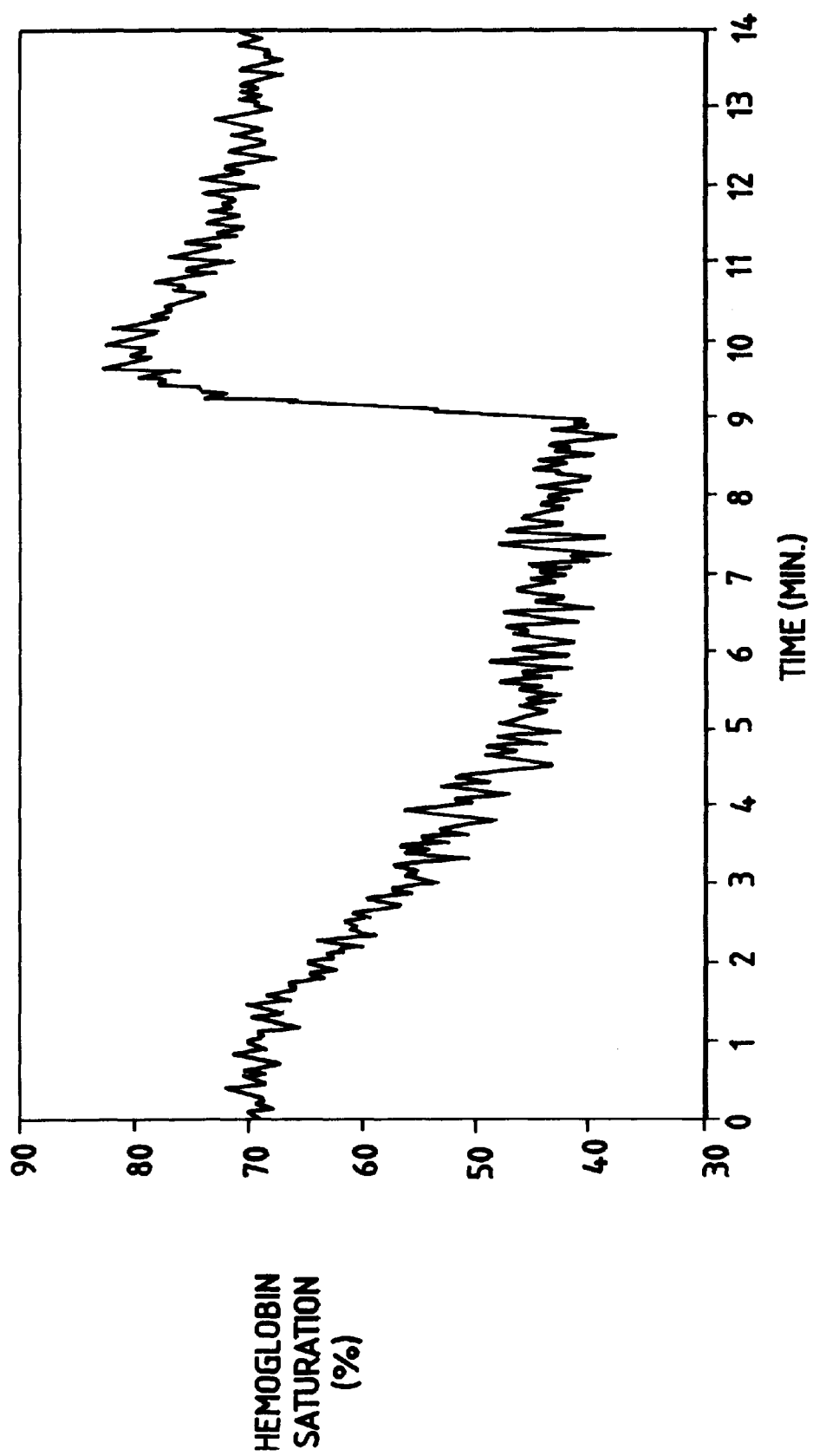
FIG. 5 is an exemplary graph showing how the apparatus of this invention is capable of determining hemoglobin saturation non-invasively in a patient in real time.

In this specific embodiment, accurate values of tissue oxygenation can be obtained in a fraction of a second. Thus, a record of hemoglobin saturation for an individual patient may be provided over time, as illustrated for example in FIG. 5, by the simple application of sensor head 12 to the skin of the patient.

In similar manner, the concentration of glucose or the like can be monitored in real time without drawing blood using the scattering coefficient of the turbid medium, which may be determined by the method described above or other desired method. The scattering coefficient technique may be used to determine the relative concentration of materials that are not strongly absorbed at the wavelengths used.

Figure 6:
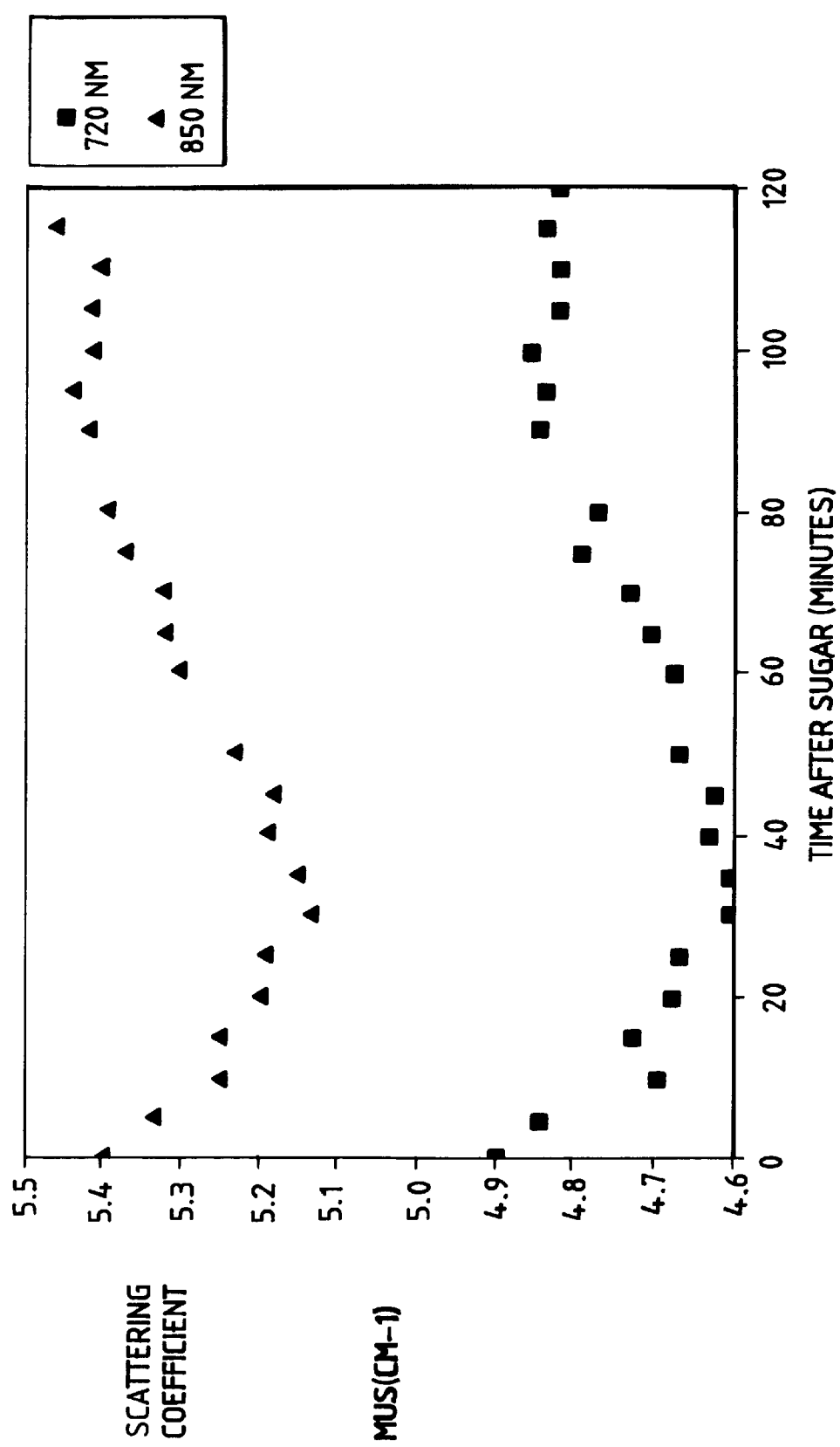
FIG. 6 is an exemplary graph showing how the apparatus of FIGS. 1–4 is capable of determining glucose levels non-invasively in a patient in real time.

Referring to FIG. 6, the graph shown represents the data obtained on the group of human volunteers. The volunteers drank amount of glucose representing 2 grams of glucose per kg of body weight then, using apparatus described in this invention, the scattering coefficient was monitored at regular intervals for two hours, with a typical run being shown as FIG. 6. Two curves of data points are shown, the triangular data points being taking with infrared light at 850 nm and the other data points being taken with infrared light at 720 nm.

The zero point time represents the original scattering coefficient achieve on the head 12 of the photometric unit is placed on the thigh of the patient. After injection of the glucose, the scattering coefficient drops substantially to a minimum, and then arises at a slower rate back to a value which is approximately the same as the original value. The slight "rebound" of the scattering coefficient is 850 nm may indicate a psychological response to the load of sugar, resulting in a slight decrease in the normal blood sugar level.

From these data, it can seen that the blood glucose level of volunteers can be monitored on a real time basis by monitoring of the scattering coefficient of light passing through a portion of the body of the patient.

Figure 7:
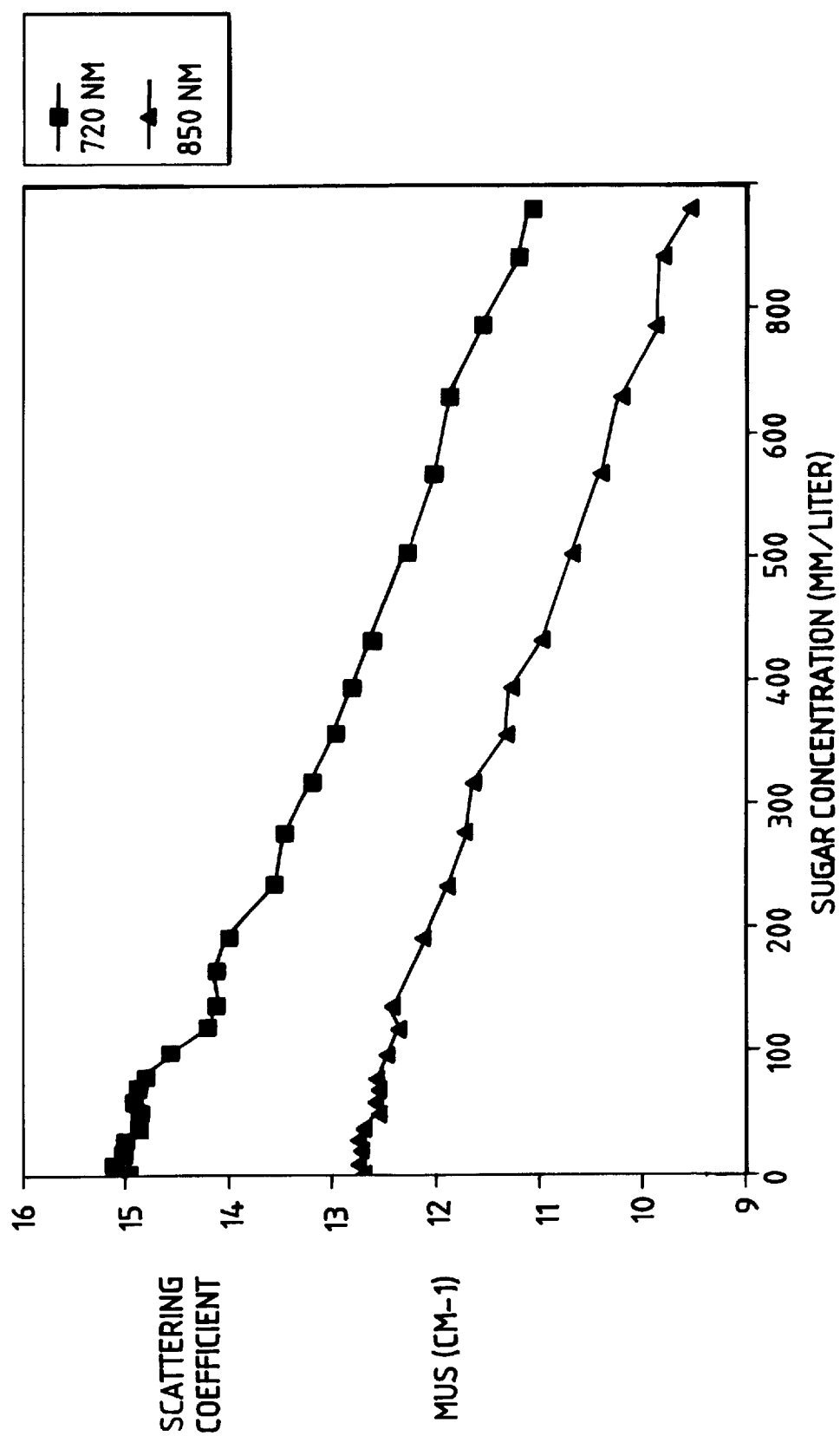
FIG. 7 is a graph showing the relation of the scattering coefficients at two wavelengths in an intravenous fat emulsion as the glucose concentration is increased.

Referring to FIG. 7, an intravenous fat emulsion (Intralipid Brand Fat Emulsion) is provided with increasing concentrations of dissolved glucose as shown. The scattering coefficient of light through the fat emulsion-sugar solution was determined at a variety of known concentrations, and is shown to decrease in a predictable manner dependent upon the concentration of the glucose present.

It is not necessary to use all of the light sources 22, 24 in every procedure of the apparatus of this invention. More light sources, for example 16 or 32, may be used. Also, a multiplexing principle may be applied to a much larger number of light sources, if desired, for the simultaneous determination of the concentration of more metabolites, or other metabolites from data which is more difficult to acquire. If a fewer number of light sources are used than 4 or 8, the rate of data acquisition can be increased accordingly. A higher acquisition rate can allow the determination of signals correlated with heart and breathing rhythms.

If desired, a pair of detector heads may be provided to process signals from differing detectors or sensors 26 positioned at different locations on the body, or at different sampling rates, so that fast and slow processes can simultaneously be measured.

Cross correlation frequencies used herein may typically vary from about 40 Hz to about 4000 Hz with relatively comparable results. The use of higher values for a cross-correlation frequency allows better detection of faster processes.

While the light source multiplexer of FIG. 4 was constructed in this embodiment using mechanical relays, solid state switches may be used as a substitute if there is a desire to sequentially illuminate the respective lights 22, 24 at a rate faster than 2.5 milliseconds.

The respective light sources should be calibrated to give comparable light intensities at the detector 26. This may be done by the addition of series resistors to decrease the current in some of the light sources as needed. Light source equilibration permits the use of all the dynamic range of an analogue-to-digital converter, and may be done at the time of construction of the instrument.

However, it is desirable to periodically check the light source calibration for drifts over long use in the light source illumination characteristics. This calibration may be performed by placing head 12 on a solid block of a substance of known absorption and scattering coefficients, to determine the intensity of each light source as sensed by sensor 26. Note that this calibration procedure is different from the calibration of the present commercial oxymeters that need to be calibrated according to certain statistical tables based on the photometric characteristics of the particular tissue to be measured. The calibration that should be periodically accomplished in the instruments of this invention is a simple measurement of the light emission characteristics of the respective lights 22, 24, and nothing more.

The instrument of this invention permits direct, on screen, simultaneous monitoring in real time of several tissue parameters such as tissue oxygenation and total blood volume. Other physiologically important parameters such as blood flow and oxygen consumption can be computed as well from the independently determined concentration of oxyhemoglobin and deoxyhemoglobin, and the timed dependance of such parameters directly during a medical procedure, surgical operation, or the like.

The instrument described above in accordance with this invention utilizes the distance dependence of at least two out of three of the DC, AC, and phase shift values to calculate the scattering and absorption coefficients, preferably at two different wavelengths. The data obtained by this invention can also be used with different algorithms from that disclosed above to obtain desired information.

Both frequency synthesizer card 25 and data acquisition card 40 may basically be of the type described in the previously cited patents. Modifications of these cards for purposes of this invention may be readily accomplished by those skilled in the art.

The above has been offered for illustrative purposes only, and is not intended to limit the scope of the invention of this application, which is as defined in the claims below.

That which is claimed:

1. The method of determining parameters of a highly scattering medium, which comprises:

passing at least two groups of modulated beams of light, each group being of a single wavelength, through differing distances of said medium, said beams of light being modulated at a first frequency, each group of light beams comprising light of a wavelength which is different from the wavelength of the other group;

detecting said beams of light which transverse said medium using at least one light sensor, modulated at a second frequency that is different from said first frequency but phase-coherent with said modulated light;

deriving at a third frequency resultant signals from said light beams detected at said second frequency, said third frequency being the difference between said first frequency and said second frequency; determining data comprising at least two of phase shift, DC and AC components of said light; an determining a parameter of said medium from said data, said method being free of a step of comparing said beams of light which traverse said medium with beams of said light as emitted prior to transverse said medium.

2. The method of claim 1 in which said beams of light as emitted prior to transversing said medium are not measured.

3. The method of claim 1 comprising the step of determining slopes of at least two of said phase shift, DC, and AC components of said light detected from the resultant signals derived from said light beams of differing distances and determining at least one an absorption coefficient and a scattering coefficient of said medium from said slopes.

4. The method of claim 3 comprising the step of determining an absolute concentration in said medium of at least one form of hemoglobin from said absorption coefficient.

5. The method of claim 3 comprising the step of determining a relative concentration of glucose in said medium from said scattering coefficient.

6. The method of claim 1 in which each of said wavelengths is at an absorption frequency of one different material of a pair of materials in said scattering medium, each of said wavelengths being substantially transparent to the other of said pair of materials.

7. The method of claim 1 in which said highly scattering medium is living tissue.

8. The method of claim 1 in which the wavelength of said light is about 650 nm. to about 1,000 nm., the intensity of light from said light sources being amplitude modulated at said first frequency of 10 to 500 MHz., and the second frequency differs from said first frequency by about 10 Hz–100 Hz.

9. The method of sample analysis which comprises:

sequentially illuminating and shutting off a plurality of light sources which are spaced at different distances from at least one light sensor to provide differing light path lengths from light source to light sensor through said sample, while modulating the intensity of light from said light sources at a first frequency, and also passing said modulated light path lengths through a highly scattering sample for testing and then to said at least one sensor; deriving resultant signals from the sensor as a function of said light beams of differing path lengths passing through said highly scattering sample; and determining at least two of phase shift, DC, and AC components of said light as sensed by the sensor compared with the modulated light as originally emitted by the light sources, said method being free of direct measurement of the light as originally emitted by the light sources.

10. The method of sample analysis which comprises:

sequentially illuminating and shutting off a plurality of light sources which are spaced at different distances from at least one light sensor while modulating the intensity of light from said light sources at a first frequency, while also passing said modulated light through a highly scattering sample for testing and then to said at least one sensor;

providing a signal coherent with said modulated light at a second frequency to said at least one light sensor;

modulating the gain of, or multiplying the output of, said at least one light sensor by said coherent signal, said second frequency being different from said first frequency; and driving resultant signals from the at least one sensor while sequentially receiving said modulated light from said plurality of light sources, said resultant signals being at a frequency of the difference between the first and second frequencies; and determining at least two of phase shift, DC and AC components of said modulated light as sensed by the at least one sensor, compared with the modulated light as originally emitted by the light sources, said method being free of a step of directly comparing beams of light which transverse said highly scattering sample with beams of light as emitted prior to traversing said highly scattering sample.

11. The method of claim 10, in which each of said plurality of light sources is sequentially illuminated for a length of time that is an exact multiple of a wave period having a frequency which comprises the difference between said first and second frequencies.

12. The method of claim 11, in which information sensed by each light sensor from each light source is summed and averaged from about 8 to about 800 times to obtain an intensified average of the photometric information received from each light source.

13. The method of claim 12, in which said light sources comprise at least two groups, each group of light sources emitting light of the same wavelength, the light sources of different groups emitting light of different wavelengths.

14. The method of claim 10, in which said light sources comprise at least two groups, each group of light sources emitting light of the same wavelength, the light sources of different groups emitting light of different wavelengths.

15. The method of determining parameters of a highly scattering medium, which comprises:

passing modulated ligt waves through said highly scattering medium; measuring the effect of said highly scattering medium on said light waves as a function of source detector distance; and determining at least one of absorption and scattering parameters of said highly scattering medium in accordance with diffusion theory mathematics, using the properties of said modulated lightwaves as a function of source detector distance.

16. The method of claim 15, in which the concentration of a component of said highly scatering medium is quantitatively determined by the passing of modulated light waves of two different frequencies through said highly scattering medium, the properties of said light waves of two different wavelengths being measured as a function of source detector distance.

17. The method of claim 16 in which each of said wavelengths is at an absorption wavelength of one different material of a pair of materials in said scattering medium, each of said wavelengths being substantially transparent to the other of said pair of materials.

18. The method of claim 15 in which frequency domain parameters of said modulated beams of light are measured at a plurality of distances of light beam travel through said highly scattering medium.

19. The method of claim 15 in which said highly scattering medium is living tissue.

* * * * *